(12) United States Patent
Biggs et al.

(10) Patent No.: US 8,546,642 B2
(45) Date of Patent: Oct. 1, 2013

(54) ABSORBENT ARTICLE WITH SLITTED ABSORBENT CORE

(75) Inventors: Jehann Biggs, Philadelphia, PA (US); Raquel Carbonari, Philadelphia, PA (US)

(73) Assignee: SCA Hygiene Products AB, Goteborg (SE)

( * ) Notice: Subject to any disclaimer, the term of this patent is extended or adjusted under 35 U.S.C. 154(b) by 801 days.

(21) Appl. No.: 12/695,840

(22) Filed: Jan. 28, 2010

(65) Prior Publication Data

US 2011/0184364 A1 Jul. 28, 2011

(51) Int. Cl.
*A61F 13/15* (2006.01)

(52) U.S. Cl.
USPC ............... 604/383; 604/385.101; 604/385.01

(58) Field of Classification Search
USPC ............... 604/838, 385.01, 385.101, 385.16, 604/385.201
See application file for complete search history.

(56) References Cited

U.S. PATENT DOCUMENTS

| | | | |
|---|---|---|---|
| 5,139,861 A | 8/1992 | Williams et al. | |
| 5,476,711 A | 12/1995 | Hebbard et al. | |
| 5,846,231 A * | 12/1998 | Fujioka et al. | 604/380 |
| 5,944,706 A | 8/1999 | Palumbo et al. | |
| 6,046,377 A | 4/2000 | Huntoon et al. | |
| 6,506,961 B1 * | 1/2003 | Levy | 604/380 |
| 6,706,943 B2 | 3/2004 | Onishi et al. | |
| 6,899,701 B2 * | 5/2005 | Carstens et al. | 604/385.01 |
| 7,510,988 B2 * | 3/2009 | Wada et al. | 442/375 |
| 7,550,646 B2 * | 6/2009 | Tamura et al. | 604/380 |
| 7,857,797 B2 * | 12/2010 | Kudo et al. | 604/385.01 |
| 7,888,549 B2 * | 2/2011 | Jansson et al. | 604/380 |
| 8,034,991 B2 * | 10/2011 | Bruzadin et al. | 604/378 |
| 2003/0119402 A1 | 6/2003 | Melius et al. | |
| 2004/0243084 A1 | 12/2004 | Yoshimasa et al. | |
| 2005/0004547 A1 | 1/2005 | Lavash | |
| 2005/0045296 A1 | 3/2005 | Adam et al. | |
| 2005/0148964 A1 | 7/2005 | Chambers, Jr. et al. | |
| 2006/0047257 A1 | 3/2006 | Raidel et al. | |
| 2006/0189954 A1 | 8/2006 | Kudo et al. | |
| 2007/0135787 A1 | 6/2007 | Raidel et al. | |
| 2007/0244455 A1 | 10/2007 | Hansson et al. | |

FOREIGN PATENT DOCUMENTS

| | | |
|---|---|---|
| EP | 0 210 968 | 2/1987 |
| EP | 0 635 275 | 1/1995 |
| EP | 1 154 937 | 9/2004 |

(Continued)

OTHER PUBLICATIONS

International Search Report and Written Opinion of the International Search Authority dated May 25, 2011 in PCT/US2011/021987 filed Jan. 21, 2011.

(Continued)

*Primary Examiner* — Lynne Anderson
(74) *Attorney, Agent, or Firm* — Drinker Biddle & Reath LLP (57) ABSTRACT

An absorbent article, such as a sanitary napkin, includes a top sheet and a back sheet with a resilient, composite absorbent core sandwiched therebetween. To decrease the stiffness, the absorbent core includes an outer line and an inner line on each side of a longitudinal centerline. The outer line includes a plurality of slits having spaces therebetween, and the outer line extends convexly when viewed from the longitudinal centerline. The plurality of slits in the absorbent core impart better bending ability of the absorbent article, particular for stiff airlaid absorbent cores.

26 Claims, 7 Drawing Sheets

(56) References Cited

FOREIGN PATENT DOCUMENTS

| | | |
|---|---|---|
| EP | 1 023 021 | 11/2005 |
| EP | 1 634 556 | 3/2006 |
| WO | WO-9507674 A2 | 3/1995 |
| WO | 99/16399 | 4/1999 |
| WO | WO-9958092 A1 | 11/1999 |
| WO | 00/34567 | 6/2000 |
| WO | 03/099182 | 4/2003 |
| WO | 2005/041815 | 5/2005 |
| WO | WO-2007049725 A1 | 5/2007 |
| WO | 2009/047596 | 4/2009 |

OTHER PUBLICATIONS

Written Opinion of the International Search Authority dated Feb. 2, 2012 in PCT/US2011/021987 filed Jan. 21, 2011.

* cited by examiner

ABSORBENT ARTICLE WITH SLITTED ABSORBENT CORE

FIELD OF THE INVENTION

The present invention pertains to an absorbent article having a resilient absorbent core. More particular, the present invention pertains to an absorbent article having a resilient absorbent core with a plurality of slits.

BACKGROUND OF THE INVENTION

Absorbent articles for absorption of body fluids are available in a number of different designs. For absorption of urine and excrement, use is generally made of diapers or incontinence guards. There are other types of absorbent articles, such as feminine hygiene products and incontinence guards. These products typically include a top sheet facing the body of the user, a back sheet facing the garment of a user, and an absorbent layer sandwiched between the inner, top sheet and outer, back sheet.

With prior art hygiene products, the absorbent core has been made of bulky fluff pulp/SAP material by mat forming. However, a drawback to these types of cores is a lack of integrity. As such, there has been a movement towards the use of thinner, higher SAP content cores. In some situations, the typical mat formed absorbent cores are totally replaced by highly compressed air laid structures. For example, U.S. Patent Publication No. 2005/0045296 describes an airlaid composite core with pulp, superabsorbent and bicomponent binder fibers.

However, one drawback to using airlaids in moderate to heavy absorbency incontinence pads is that these pads tend to be very stiff when the basis weight is increased and the thickness is decreased. U.S. Patent Publication No. 2004/0243084 discloses an absorbent product with folding lines made of point shaped compressions. However, the point shaped compressions do not reduce the bending resistance sufficiently when a stiff airlaid composite core is used.

In addition, to solve the issue of stiffness and bunching in the prior art, absorbent cores have been made in an hour glass shape to help it better conform. A drawback to this design is that the edges of the absorbent core must be cut away, thereby wasting core material.

Accordingly, there is a need in the art for an absorbent product having a resilient composite core which is less stiff and conforms better to the body of the user, and does not waste core material.

SUMMARY

According to a first aspect of the present invention, an absorbent product comprises a backsheet, a topsheet, and an absorbent core therebetween, wherein the absorbent core includes an inner line and an outer line on each side of a longitudinal centerline. Each of the inner lines and outer lines including a plurality of slits having spaces therebetween. Each of the outer lines extend convexly when viewed from the longitudinal centerline.

According to a second aspect of the present invention, an absorbent product comprises a backsheet, a topsheet, and an absorbent core therebetween. The absorbent core includes an outer line on each side of a longitudinal centerline. Each of the outer line including a plurality of slits having spaces therebetween and extending convexly when viewed from the longitudinal centerline.

Yet another feature of the present invention pertains to an absorbent product wherein the length of the slits are greater in the outer lines than in the inner lines. This further feature applies to the first aspect described above.

Yet another feature of the present invention pertains to an absorbent product wherein the lengths of the slits in the outer line are between about 3 mm to 15 mm and spaces between the slits are between about 2 mm to 8 mm, the length of the slits in the inner line are between about 3 mm to 8 mm and spaces between the slits are between about 2 mm to 5 mm. This further feature applies to the first aspect described above.

Yet another feature of the present invention pertains to an absorbent product wherein the lengths of the slits are greater than the spaces between the slits. This further feature applies to the first aspect and second aspect described above.

Yet another feature of the present invention pertains to an absorbent product wherein a shortest distance from the longitudinal center line to the outer line is at least about 15 mm and a shortest distance from the longitudinal center line to the inner line is at least about 10 mm. This further feature applies to the first aspect described above.

Yet another feature of the present invention pertains to an absorbent product wherein the outer line is shaped as a crescent and has a longitudinal distance from a starting position to an ending position of between about 70 mm to 200 mm, and more preferably between about 80 mm to 150 mm. This further feature applies to the first aspect and second aspect described above.

Yet another feature of the present invention pertains to an absorbent product wherein one or both of the outer line and the inner line are shaped as crescents. This further feature applies to the first aspect described above.

Yet another feature of the present invention pertains to an absorbent product wherein the absorbent core has generally straight longitudinal sides that extend in parallel with the longitudinal center line. This further feature applies to the first aspect and second aspect described above.

Yet another feature of the present invention pertains to an absorbent product wherein a width of the core is between about 60 mm to 120 mm. This further feature applies to the first aspect and second aspect described above.

Yet another feature of the present invention pertains to an absorbent product wherein the absorbent core has a thickness of between about 2 mm to 10 mm and a density of between about 0.04 g/cm$^3$ to 0.50 g/cm$^3$. This further feature applies to the first aspect and second aspect described above.

Yet another feature of the present invention pertains to an absorbent product wherein a basis weight of the absorbent core basis weight of about between 350 to 1000 g/m$^2$. This further feature applies to the first aspect and second aspect described above.

Yet another feature of the present invention pertains to an absorbent product wherein the absorbent core is an airlaid core composite made from pulp, SAP, binder fibers and/or latex binder. This further feature applies to the first aspect and second aspect described above.

Yet another feature of the present invention pertains to an absorbent product wherein the absorbent product is an incontinence pad or a sanitary napkin. This further feature applies to the first aspect and second aspect described above.

Yet another feature of the present invention pertains to an absorbent product wherein lengths of the slits in the outer line are between about 3 mm to 15 mm and the spaces between the slits are between about 2 mm to 8 mm. This further feature applies to the first aspect and second aspect described above.

Yet another feature of the present invention pertains to an absorbent product wherein a shortest distance from the longitudinal center line to the outer crescent is at least about 10 mm. This further feature applies to the first aspect and second aspect described above.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 11 (A) and (B) illustrate an S-shaped slit according to the features of the present invention.

FIGS. 12 (A) and (B) illustrate an angled slit according to the features of the present invention.

DETAILED DESCRIPTION OF THE PREFERRED EMBODIMENTS

The present invention pertains to an absorbent article. An absorbent article is defined as an article or garment used for the absorption of body fluids, including but not limited to, infant diapers and training pants, adult incontinence products, feminine hygiene products, gender specific absorbent products, and pet training absorbent articles. While the preferred embodiment illustrates an incontinence pad, it should be understood that the present invention pertains to all types absorbent articles.

Figure 1:
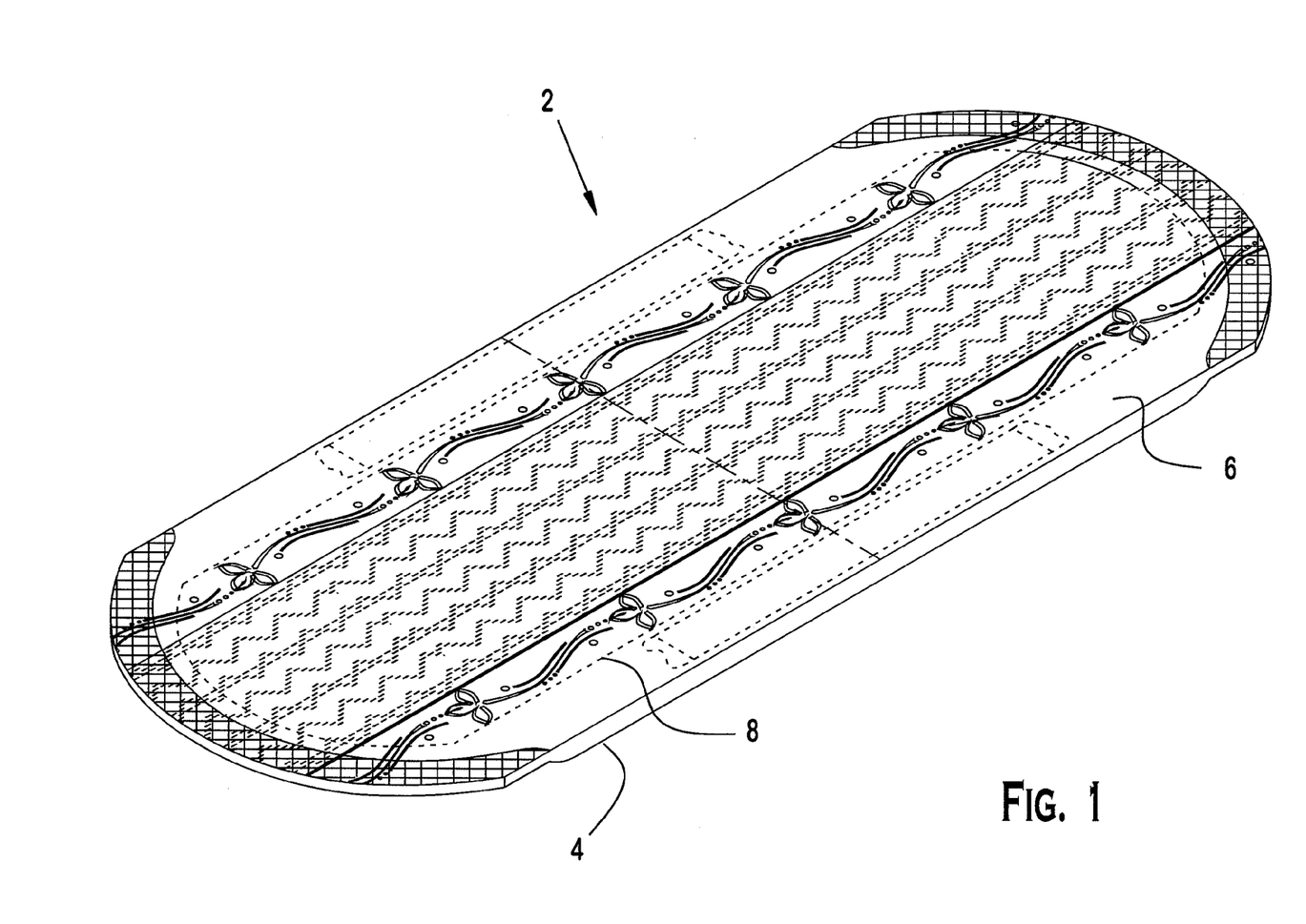
FIG. 1 illustrates a perspective view of an exemplary absorbent article according to the features of the present invention.
Figure 2:
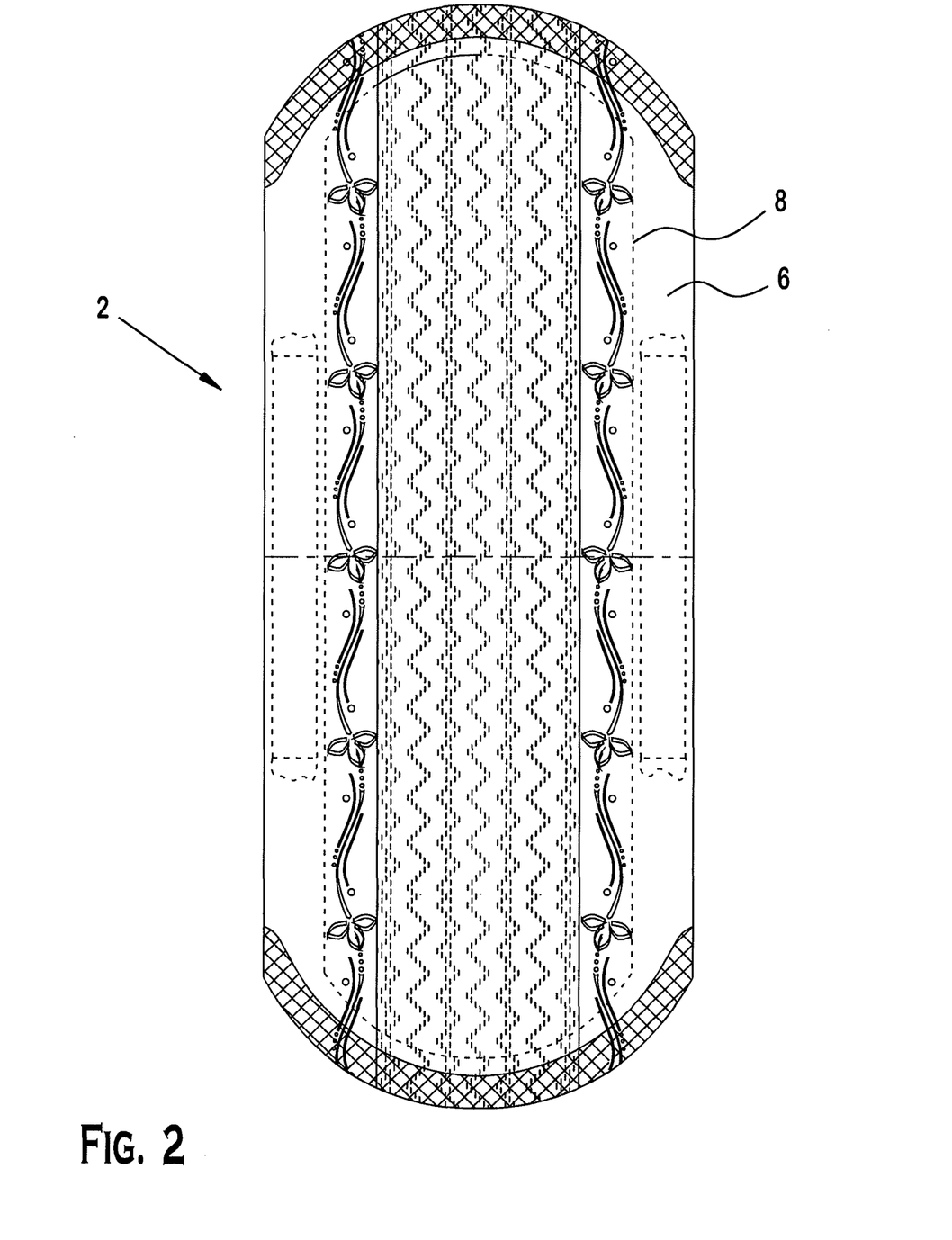
FIG. 2 illustrates a plan view of an exemplary absorbent article according to the features of the present invention.

With reference to FIGS. 1 and 2, an absorbent article 2 includes a back sheet 4 and a top sheet 6 which sandwich an absorbent core 8 therebetween. The topsheet 6 can be joined together with the backsheet 4 and the absorbent core 8, for example by means of adhesive, ultrasonic joining or by means of some form of thermal bonding.

Preferably, the absorbent core 8 is appropriately manufactured from a suitable fiber material in the form of natural or synthetic fibers having absorbent properties, or a mixture of natural fibers and synthetic fibers or other absorbent materials of a previously disclosed kind that are suitable for use in sanitary towels, incontinence pads and panty liners, for example.

The absorbent core 8 can also contain a predetermined proportion of superabsorbent polymers (SAP). SAP materials are in the form of particles, fibers, flakes or similar, and have the capacity to absorb and to chemically bind liquid equivalent to several times their own weight while forming an aqueous gel. This provides a very high water-absorbent capacity in the finished product. Preferably, the absorbent core 8 includes 30-90% SAP, with an basis weight of about between 350 to 1000 $g/m^2$, and most preferably between about 400 to 1000 $g/m^2$. In addition, the absorbent core 8 may be an airlaid core composite made from pulp, SAP and binder fibers, and/or latex binder. The absorbent core 8 may have a thickness of between about 2 mm to 10 mm and a density of between about 0.04 $g/cm^3$ to 0.50 $g/cm^3$.

For all test in the application the test pieces are conditioned in a climate of 23° C.±1° C. and 50% relative humidity±10% for 24 hours. The thickness of the product/product part, e.g. core is measured with a pressure of 0.5 kPa±0.002 kPa. The thickness is measured at 3 sites of the product/product part at the front, rear and center of the product. The average of the measurement will be the thickness of the product/product part. The basis weight of the core is measured by cutting out a sample of predetermined size and weighing the sample. By dividing the weight of the sample with the area of the basis weight is achieved. The density of a product/product part is the basis weight divided by the average thickness of the product/product part core.

The airlaid core is at least partly stabilized by the binder fibers. As described above, the present invention is particularly applicable to absorbent cores which are dense yet thin, thereby causing the core to be very stiff.

The liquid-permeable topsheet 6 includes one or more layers of one or more of the following materials: a fibrous material, for example a soft nonwoven material, plastic film, mesh, open-celled foam, material laminate, etc. The topsheet 6 may include a perforated plastic film, for example, a thermoplastic plastic material such as polyethylene or polypropylene, or a mesh-like layer of synthetic or textile material. Synthetic mono-, bi-, or multi-component fibers, made of polymers such as polyethylene, polypropylene, polyester, nylon or the like, are preferably used as a nonwoven material. Mixtures of different types of fibers can also be used for the aforementioned nonwoven material.

The backsheet 4 is preferably liquid-impermeable (or at least possesses high resistance to penetration by liquid) and is thus so arranged as to prevent any leakage of excreted fluid from the product. The backsheet 4, on the other hand, may also be vapor-permeable. For this purpose, the backsheet 4 may be manufactured from a liquid-impermeable material which includes a thin and liquid-proof plastic film. For example, plastic films of polyethylene, polypropylene or polyester can be used for this purpose. Alternatively, a laminate of nonwoven and plastic film or other suitable layers of material can be used as a liquid-proof backsheet 4. In a previously disclosed manner, the clothing side of the backsheet 4 can be provided with beads of adhesive or some other previously disclosed attachment means, which can then be utilized for the application of the product to an item of clothing. The product can also be provided with wings, that is to say folding flaps which are arranged along the sides of the product and can be utilized in conjunction with the application of the product.

Figure 3:
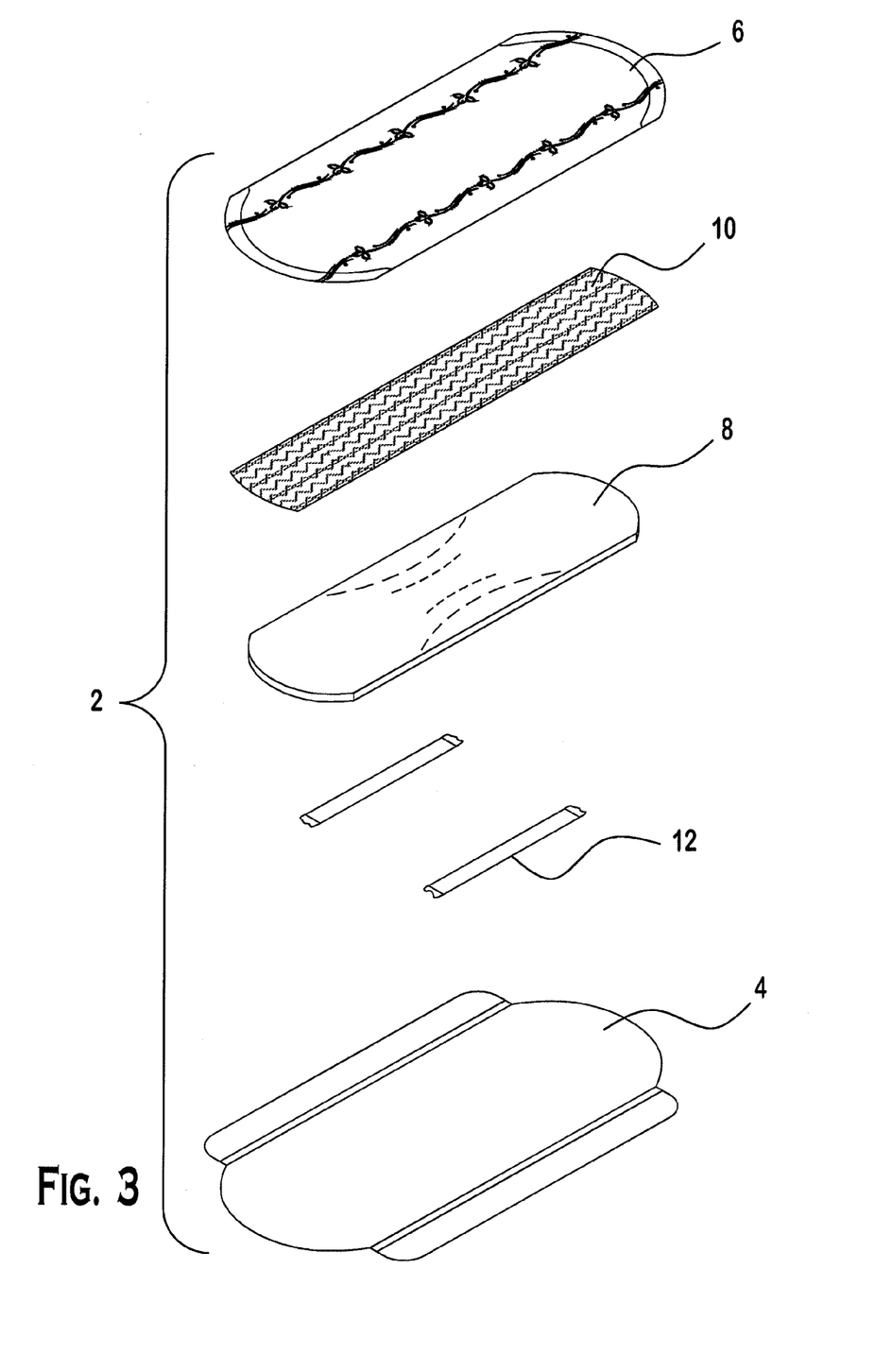
FIG. 3 illustrates an exploded view of an exemplary absorbent article according to the features of the present invention.

With reference to FIG. 3, the absorbent article 2 of the present invention is illustrated in an exploded view. In particular, an acquisition/distribution layer 10 may be disposed between the topsheet 6 and the absorbent core 8, and elastics 12 may be preferably disposed between the topsheet 6 and the backsheet 4 along longitudinal sides of the absorbent article 2. The acquisition/distribution layer 10 may be in the form of a wadding material having an appropriately specified thickness and resilience. The acquisition/distribution layer 10 may be made materials other than wadding material, such as air-laid material. The acquisition/distribution layer 10 may also incorporate fibrous materials in order to impart an appropriately balanced rigidity to it. The acquisition/distribution layer 10 can also incorporate an appropriate quantity of thermoplastic fibers in order to permit ultrasonic welding.

The absorbent article 2 may be made from numerous other layers, as is known in the art. However, the specific layers used may vary, depending on design preference and application. For example, other layers not shown may be used, such as an additional back sheet, or any other intervening layer, such as SMS (Spunbond MeltBlown Spunbond), SSS (three layers of Spunbond), Carded NW, Hydroentangled, and the like. Likewise, the particular number and order of layers is optional, depending on application and design preference.

With reference to FIGS. 4-10, various embodiments of the absorbent core 8 of the present invention will be described in more detail. Generally, the absorbent core 8 includes a longitudinal centerline 14 and longitudinal side edges 16. The absorbent core 8 can exhibit different forms, for example an essentially elongated and rectangular form, or alternatively some other more irregular form, for example hourglass or triangular form. Preferably, the longitudinal side edges 16 are substantially straight, but may also be rounded. For example, the absorbent core 8 may have generally straight longitudinal sides than extends in parallel with the longitudinal centerline 14. Preferably, a width of the core is about between 60-120 mm.

Figures 5, 5A:
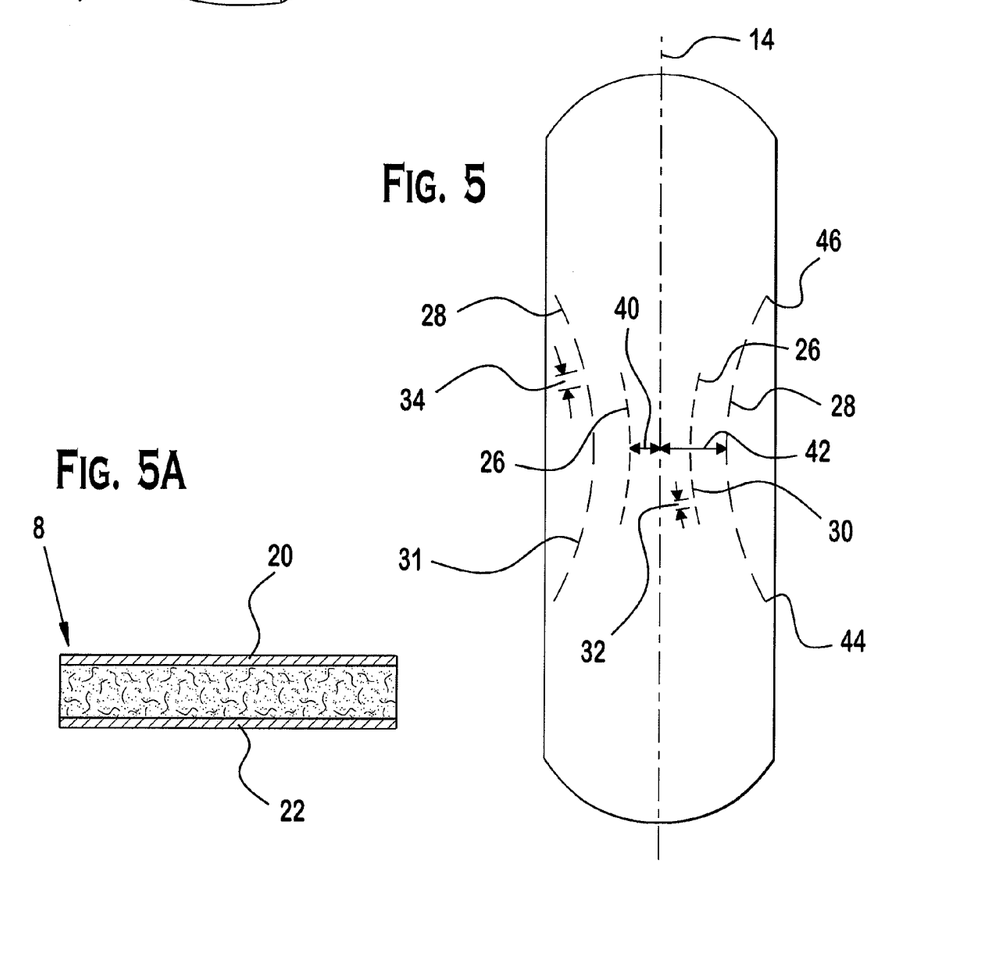
FIG. 5 illustrates a plan view of an exemplary absorbent core according to the features of the present invention.
FIG. 5A is a cross sectional view of the absorbent core showing a top layer and a bottom layer.
Figure 5B:
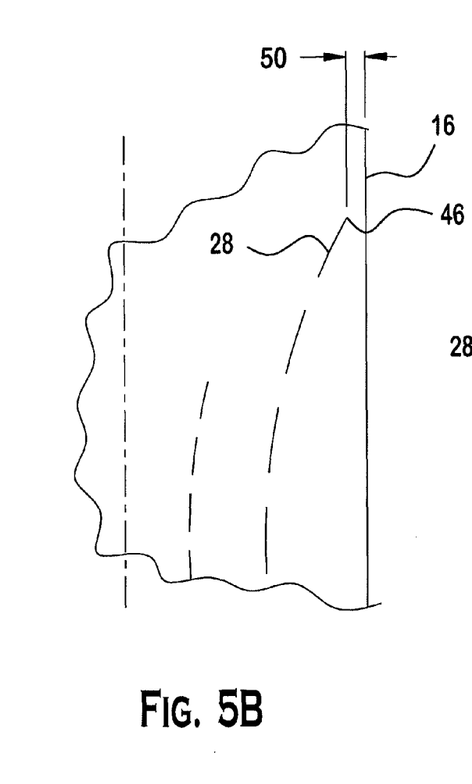
FIG. 5B is a closer view of the absorbent core of FIG. 5, showing spacing between the longitudinal side edge and slit closest to the longitudinal side edge.

With reference to FIG. 5A, a cross section of the absorbent core 8 is illustrated. Preferably, the absorbent core 8 includes a top layer 20 at the top sheet side and/or a bottom layer 22 at the back sheet side. Preferably, the top layer 20 is made of pulp and partly melted binder fibers, and the bottom layer 22 is made of tissue. However, the top layer 20 may also be made of tissue and the bottom layer 22 may be made of pulp and partly melted binder fibers and possibly also a tissue layer, depending on application or design preference. In the latter case, the tissue layer of the bottom layer is applied on the clothing side.

Figure 4:
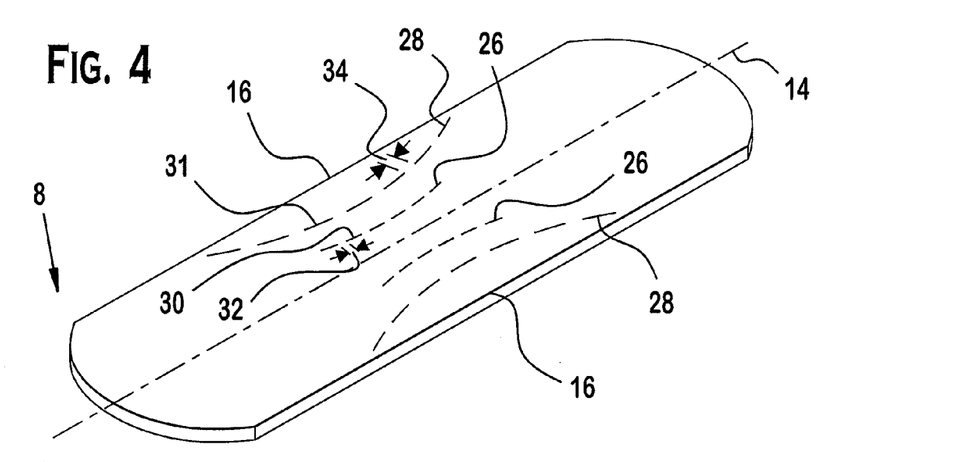
FIG. 4 illustrates a perspective view of an exemplary absorbent core according to the features of the present invention.

With reference to FIGS. 4 and 5, a first embodiment of the absorbent core 8 will be described in more detail. The absorbent core 8 includes an inner line 26 and an outer line 28 on each side of a longitudinal centerline 14. Each of the inner lines 26 and outer lines 28 include a plurality of slits 30 and 31, respectively, having spaces 32 and 34, respectively, therebetween. In the preferred embodiment, the inner lines 26 and outer lines 28 extend convexly when viewed from the longitudinal centerline 14. While only two lines are shown on each side of the longitudinal centerline 14, it should be understood that only one line is needed (described in more detail below) and that more than two adjacent lines are also possible.

The plurality of slits in the absorbent core 8 impart better bending ability of the absorbent article 2, particular for stiff absorbent cores 8, e.g., made from air laid material. As such, the positioning of the slits is important, and chosen to maximize cupping of the absorbent article 2 during use. Without the slits, the absorbent core 8 has the freedom to bend in all directions along the absorbent core 8.

Figure 6:
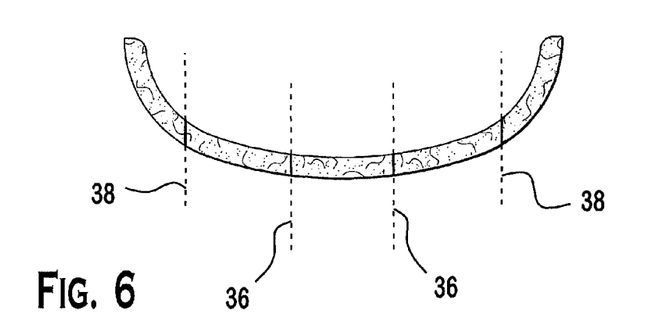
FIG. 6 illustrates a cross sectional view of the absorbent core according to FIGS. 4 and 5, highlighting its inflection points during use.
Figure 7:
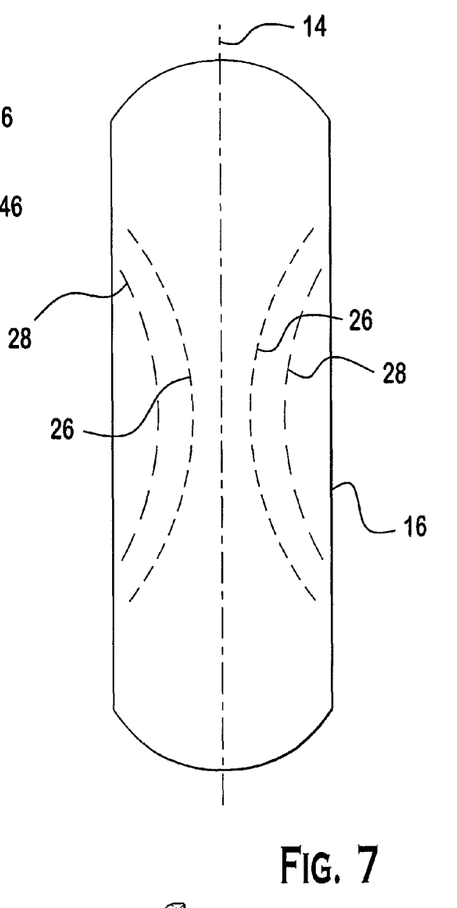
FIG. 7 illustrates a plan view of another exemplary absorbent core according to the features of the present invention.

When in use, the absorbent core 8 bends at inflection points 36 and 38. The inflection points 36 are where the inner line 26 of slits is located and the inflection points 38 are where the outer line 28 of slits is located. As shown in FIG. 6, more bending occurs at the inflection points 38 because of the larger slits, which is desired so that the core 8 naturally cups the body of a user. In addition, the slits allow for the bending forces to be located in the central region of the absorbent core 8 rather than at the ends of the absorbent article 2. That is, the central portion of the absorbent core 8 between inflection points 36 remains relatively flat so that a cup can be formed, and the sides act as barriers. Bending occurs along the bending lines and the ends of the pad maintain a neutral position. The elastics help activate the bending points to form a U-shaped appearance.

According to the features of the present invention, the bending of slits will propagate to the longitudinal edges of the absorbent core 8 and not longitudinally down the entire centerline of the pad when force is applied. However, it should be noted that if the inner lines and outer lines are too close to the longitudinal centerline, inflection happens too close to the longitudinal centerline 14 of the absorbent article, and causes sides of the article to fold in on the user.

The slits in the absorbent core 8 before use are essentially closed and are able to retain substances in the core material. Examples of substances are superabsorbents (SAP). When the product is used, the slits are influenced by the movement of the wearer in such a way that they are opened and closed, which minimizes the risk of SAP leaking out.

A "slit" is defined as an essentially one-dimensional through going opening in a layer of material having an extent in the longitudinal direction and a depth which depend on the thickness of the layer of material. The slit comprises two boundary surfaces, each deliminated by the extent of the slit in the longitudinal direction and the thickness of the layer of material. When the layer of material is unaffected by external forces, the boundary surfaces are in contact with one another and close the opening in the same way as if a slit were not to be present. However, it should be understood that a hole may be considered as a slit, even though boundary surfaces may not be in contact with one another when unaffected by external forces.

The slits are manufactured by rupturing the bonds in the layer of material over the distance requited for the extension of the slit. The bonds can be ruptured, for example, by producing an incision in the layer of material by means of slitting, cutting or in some other way. This is entirely true in a theoretical model, although in practical reality material will disappear on a micrometric scale as a consequence of for example, blunt tools, etc. Preferably, the slits are formed from a topsheet side of the absorbent core 8 toward a backsheet side so that a core material at edges of the slits is slightly depressed toward the backsheet side of the core 8.

The slits may be made in the core by means of a through going incision in the core perpendicular to a top or bottom plane surface, but it can also be made in the core by means of a through going incision at an angle to the plane surface.

The slits themselves can be straight, S-shaped, V-shaped, Z-shaped, U-shaped, or can possess any other suitable shape. The slits can also comprise combinations of different shapes, for example a plurality of straight or curved slits and having the same or a different length, where every other slit is oriented at an angle (preferably essentially 90°) in relation to the essential longitudinal extent of the preceding slit, but where the slits are situated at a distance from one another. The slits may be arranged at an angle of between 0 and 180° relative to the longitudinal centerline 14, preferably in the range from 20°-65° and/or 110°-155° in relation to the longitudinal centerline 14. Different parts of the slits can have a different direction in relation to the centerline 14.

Preferably, the lengths of the outer slits 31 and the spaces 34 therebetween in the outer line 28 are greater than the lengths of the inner slits 30 and the spaces 32 therebetween in the inner line 26. More preferably, the lengths of the slits 31 in the outer line 28 are between about 3 mm to 15 mm, most preferably between 9 mm to 11 mm, and the spaces 34 between the slits 31 are between about 2 mm to 8 mm, most preferably between 4 mm to 6 mm, the length of the slits 30 in the inner line 26 are between about 3 mm to 8 mm, most preferably between about 5 mm to 6 mm, and the spaces 32 between the slits 30 are between about 2 mm to 5 mm, most preferably between 3 mm to 4 mm. In addition, the lengths of the slits 30, 31 are preferably greater than the spaces 32, 34 between the slits, respectively. It should be understood that slits in either of the inner lines 26 and outer lines 28 may have different or the same lengths and the same applies to the length of the spaces between the slits.

Figure 11:
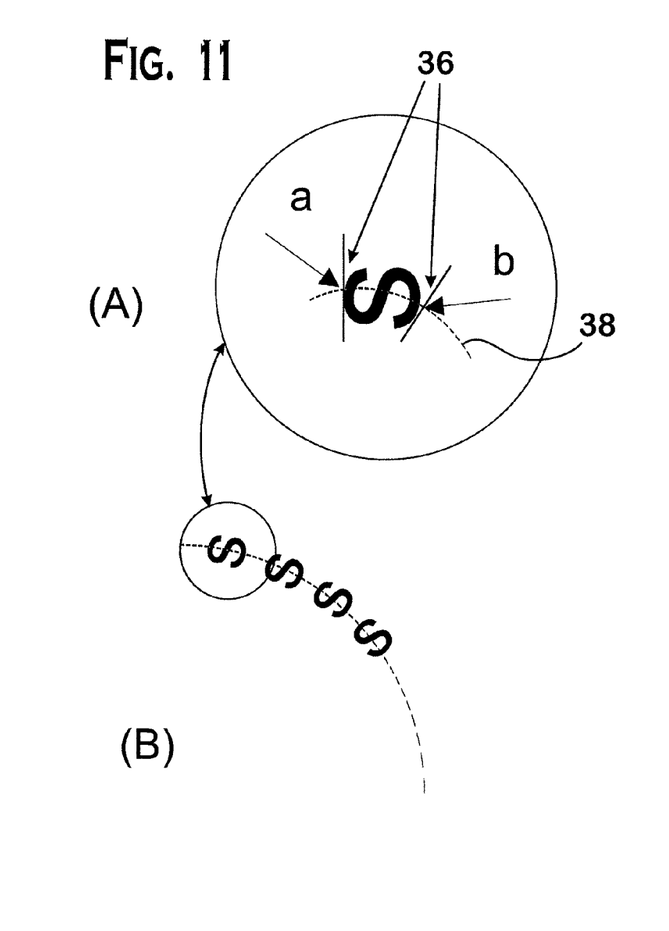
Figure 12:
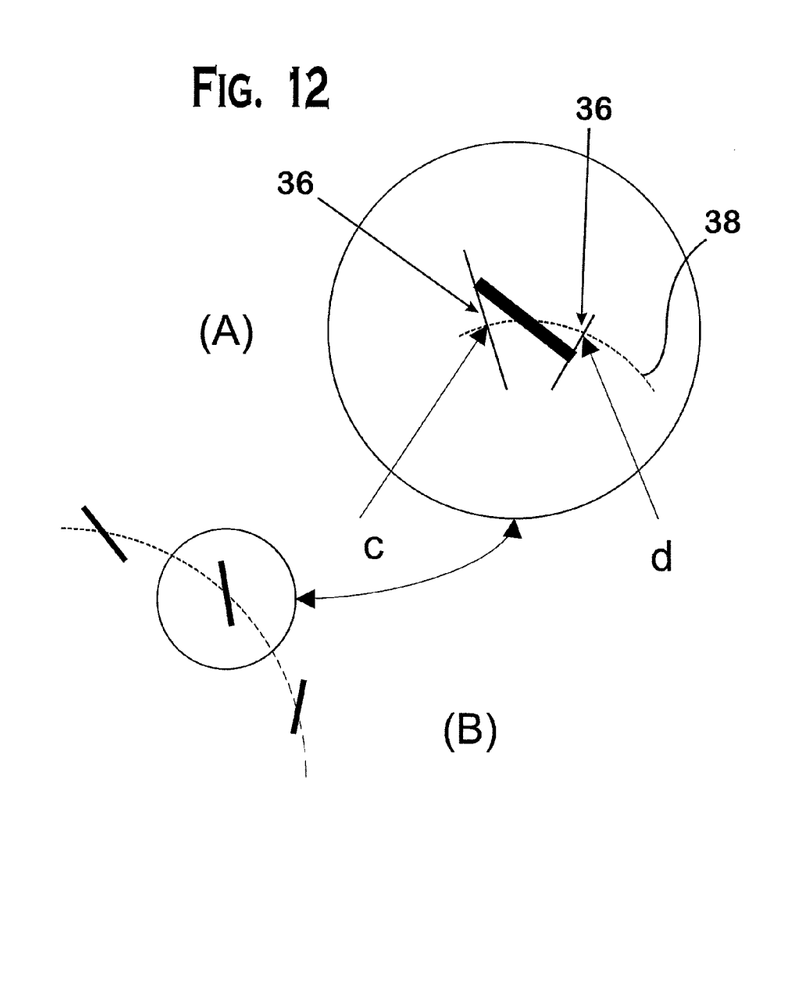

With reference to FIGS. 11 and 12, calculation of the lengths of the slits is described in more detail. In particular, the length of the slits are measured along an imaginary arc line 38 that goes through the center of the slits. The imaginary arc line 38 is chosen so that it divides the slits in half so that half of the slits are on outer side of the line and the other half on the inside. The starting point (a, c) of each slit is determined by drawing a line 36 perpendicular to the imaginary arc line 38 to the "front most" part of the slit. Similarly, the ending point (b, d) of each slit is determined by drawing a line 36 perpendicularly to the imaginary arc line 38 to the "rear most" part. The points where the lines crosses/intersect with the arc line are the starting points (a, c) or ending points (b, d). The length of the slits is measured along the curvature of the imaginary arc line 38 from a starting point (a, c) to the respective ending point (b, d). In addition, the length of the spaces between the slits is determined by measuring the length between an ending point (b, d) of one slit and the starting point (a, c) of the adjacent slit.

For example, with reference to FIG. 11, a plurality of S-shaped slits is illustrated. The length of the S-shaped slits is determined by drawing an imaginary arc line 38 through the center of the S-shaped slit, which divides the slit in half. The starting point (a) is determined by drawing a line 36 perpendicular to the imaginary arc line 38 to the "front most" part of the S-shaped slit. Similarly, the ending point (b) of each slit is determined by drawing a line 36 perpendicularly to the imaginary arc line 38 to the "rear most" part. The length of the S-shaped slit is determined by measuring along the curvature of the imaginary arc line 38 from the starting point (a) to the respective ending point (b). The length of the spaces between two adjacent S-shaped slits is determined by measuring the length between an ending point (b) of one slit and the starting point (a) of the adjacent slit.

With reference to FIG. 12, a plurality of angled slits is illustrated. The length of the angled slits is determined by drawing an imaginary arc line 38 through the center of the angled slit, which divides the slit in half. The starting point (b) is determined by drawing a line 36 perpendicular to the imaginary arc line 38 to the "front most" part of the angled slit. Similarly, the ending point (d) of each slit is determined by drawing a line 36 perpendicularly to the imaginary arc line 38 to the "rear most" part. The length of the angled slit is determined by measuring along the curvature of the imaginary arc line 38 from the starting point (c) to the respective ending point (d). The length of the spaces between two angled slits is determined by measuring the length between an ending point (d) of one slit and the starting point (c) of the adjacent slit.

With reference FIG. 5, a shortest distance 40 from the longitudinal center line 14 to the inner line 26 is at least about 10 mm and a shortest distance 42 from the longitudinal centerline 14 to the outer line 28 is at least about 15 mm. Preferably, the outer line 28 is shaped as a crescent and the inner line 26 is shaped as a crescent. More preferably, the inner line may be about 50% of the arc length of the outer line 28. It should also be understood that the outer line and the inner line may have the same radius, or different radius, depending on application and design preference.

Preferably, the longitudinal distance between a starting position 44 and ending position 46 of the outer line 28 is between about 70 mm to about 200 mm, and more preferably between about 80 mm to 150 mm. In particular, the starting position 44 and the ending position 46 may start or end directly at the longitudinal side edges 16 of the absorbent core 8 or may be spaced a short distance 50 from the longitudinal side edges 16 measured in the crosswise direction of the core 8 (see FIG. 5B), e.g., a distance equal to or smaller than the space between the slits. However, spacing the starting position 44 and ending position 46 from the longitudinal side edges 16 is preferable, because placing the slits at the longitudinal side edges 16 could cause tearing, thereby lowering the integrity of the core. Furthermore, the ends of the slit walls could chafe the skin of the wearer.

Figure 8:
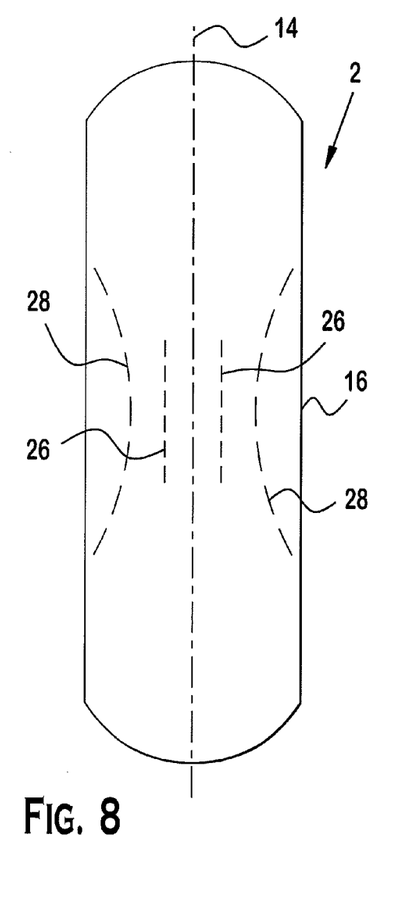
FIG. 8 illustrates a plan view of yet another exemplary absorbent core according to the features of the present invention.

As shown in FIG. 5, the inner line 26 need not extend to the longitudinal side edges 16. However, with reference to FIG. 7, the inner line 26 can extend to the longitudinal side edges. In addition, it is not necessary that the inner line 26 be curved. As shown in FIG. 8, the inner line 26 is shown as being straight, and not curved. It should be understood that the outer lines and inner lines are placed in a crotch area of the product either in the longitudinal center or offset from the longitudinal center toward the front end of the absorbent core 8. In addition, the slits may be colored.

Figure 9:
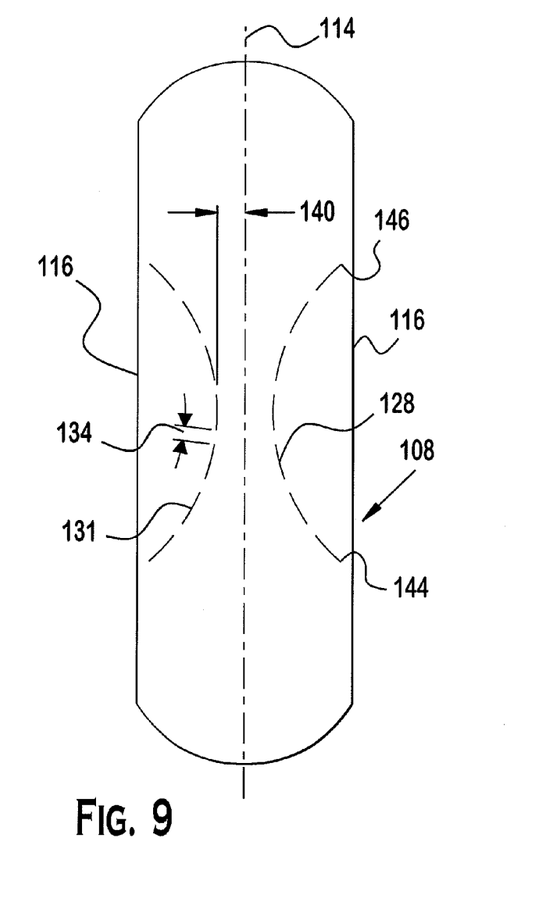
FIG. 9 illustrates a plan view of yet another exemplary absorbent core according to the features of the present invention.

With reference to FIG. 9, an alternative embodiment of the absorbent core 108 of the present invention will be described in more detail. An absorbent core 108 includes a longitudinal centerline 114 and longitudinal side edges 116. The absorbent core 108 includes only an outer line 128 on each side of a longitudinal centerline 114. Both outer lines 128 include a plurality of slits 131 spaces 134 therebetween. In the preferred embodiment, the outer lines 128 extend convexly when viewed from the longitudinal centerline 114.

Figure 10:
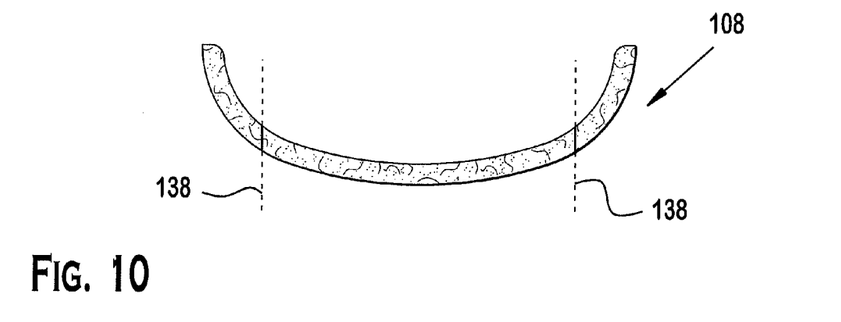
FIG. 10 illustrates a cross sectional view of the absorbent core according to FIG. 9, highlighting its inflection points during use.

With reference to FIG. 10, a cross sectional view of the absorbent core 108 is illustrated in use. When in use, the absorbent core 108 bends more at inflection points 138. The inflection points 138 are where the outer line 128 of slits is located. As shown in FIG. 10, the bending at inflection points 138 allows the absorbent core 108 to naturally cup the body of a user. In addition, the slits allow for the bending forces to be located in the central region of the absorbent core 108 rather than at the ends of the absorbent article 102. That is, the central portion of the absorbent core remains relatively flat so that a cup can be formed, and the sides act as barriers. Bending occurs along the bending lines and the ends of the pad maintain a neutral position.

The lengths, shapes and orientation of the slits described with regard to embodiments having outer and inner lines is equally applicable to the embodiment with just one line. However, the positioning of the actual outer line becomes more important. In particular, a shortest distance 140 from the longitudinal center line 114 to the outer line 128 is at least about 10 mm, and more preferably about 15 mm. Preferably, the outer line 128 is shaped as a crescent and a longitudinal distance between a starting position 144 and ending position 146 of the outer line 128 is between about 70 mm to 200 mm., and more preferably between about 80 mm to 150 mm.

The various embodiments described provide a more flexible, bendable absorbent article, particularly when using stiff airlaid composites in larger absorbency products. The slitted absorbent core 8 provides the product with extra bend ability, thereby reducing is stiffness, and advantageously cupping to the body of a user.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. An absorbent article, comprising:
   a backsheet;
   a topsheet; and
   an absorbent core therebetween, wherein the core has a thickness;
   wherein the absorbent core includes an inner line and an outer line on each side of a longitudinal centerline, each said inner lines and outer lines including a plurality of slits having spaces therebetween, each said outer line extending convexly when viewed from the longitudinal centerline, and
   wherein the plurality of slits are through going openings extending through the thickness of the core.

2. The absorbent article of claim 1, wherein the lengths of the slits are greater in the outer lines than in the inner lines.

3. The absorbent article of claim 2, wherein the lengths of the slits in the outer line are between about 3 mm to 15 mm and spaces between the slits are between about 2 mm to 8 mm, the length of the slits in the inner line are between about 3 mm to 8 mm and spaces between the slits are between about 2 mm to 5 mm.

4. The absorbent article of claim 1, wherein the lengths of the slits are greater than the spaces between the slits.

5. The absorbent article of claim 1, wherein a shortest distance from the longitudinal center line to the outer line is at least 15 mm and a shortest distance from the longitudinal center line to the inner line is at least 10 mm.

6. The absorbent article of claim 1, wherein the outer line is shaped as a crescent and has a longitudinal distance from a starting position to an ending position of between about 80 mm to 150 mm.

7. The absorbent article of claim 1, wherein the outer line is shaped as a crescent and has a longitudinal distance from a starting position to an ending position of between about 70 mm to 200 mm.

8. The absorbent article of claim 1, wherein one or both of the outer line and the inner line are shaped as crescents.

9. The absorbent article of claim 1, wherein the absorbent core has generally straight longitudinal sides that extend in parallel with the longitudinal center line.

10. The absorbent article of claim 1, wherein a width of the core is between about 60 mm to 120 mm.

11. The absorbent article of claim 1, wherein the absorbent core has a thickness of between about 2 mm to 10 mm and a density of between about 0.04 g/cm$^3$ to 0.50 g/cm$^3$.

12. The absorbent article of claim 1, wherein a basis weight of the absorbent core basis weight of about between 350 to 1000 g/m$^2$.

13. The absorbent article of claim 1, wherein the absorbent core is an airlaid core composite made from pulp, SAP, binder fibers and/or latex binder.

14. The absorbent article of claim 1, wherein the absorbent article is an incontinence pad or a sanitary napkin.

15. An absorbent article, comprising:
   a backsheet;
   a topsheet; and
   an absorbent core therebetween, wherein the core has a thickness;
   wherein the absorbent core includes an outer line on each side of a longitudinal centerline, each said outer line including a plurality of slits having spaces therebetween and extending convexly when viewed from the longitudinal centerline, and
   wherein the plurality of slits are through going openings extending through the thickness of the core.

16. The absorbent article of claim 15, wherein lengths of the slits in the outer line are between about 3 mm to 15 mm and the spaces between the slits are between about 2 mm to 8 mm.

17. The absorbent article of claim 15, wherein the lengths of the slits are greater than the spaces between the slits.

18. The absorbent article of claim 15, wherein a shortest distance from the longitudinal center line to the outer crescent is at least 10 mm.

19. The absorbent article of claim 15, wherein the outer line is shaped as a crescent and has a longitudinal distance from a starting position to an ending position of between about 80 mm to 150 mm.

20. The absorbent article of claim 15, wherein the outer line is shaped as a crescent and has a longitudinal distance from a starting position to an ending position of between about 70 mm to 200 mm.

21. The absorbent article of claim 15, wherein the absorbent core has generally straight longitudinal sides that extend in parallel with the longitudinal center line.

22. The absorbent article of claim 15, wherein a width of the absorbent core is between about 60 mm to 120 mm.

23. The absorbent article of claim 15, wherein the absorbent core has a thickness of between about 2 mm to 10 mm and a density of between about 0.04 g/cm$^3$ to 0.50 g/cm$^3$.

24. The absorbent article of claim 15, wherein a basis weight of the absorbent core is about between 350 to 1000 g/m$^2$.

25. The absorbent article of claim 15, wherein the absorbent core is an airlaid core composite made from pulp, SAP, binder fibers and/or latex binder.

26. The absorbent article of claim 15, wherein the absorbent article is an incontinence pad or a sanitary napkin.

\* \* \* \* \*